United States Patent
Kobayashi

(10) Patent No.: US 10,861,197 B2
(45) Date of Patent: Dec. 8, 2020

(54) RADIOGRAPHING APPARATUS, RADIOGRAPHING SYSTEM, RADIOGRAPHING METHOD, AND STORAGE MEDIUM

(71) Applicant: CANON KABUSHIKI KAISHA, Tokyo (JP)

(72) Inventor: Tsuyoshi Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 160 days.

(21) Appl. No.: 15/782,316

(22) Filed: Oct. 12, 2017

(65) Prior Publication Data
US 2018/0108156 A1 Apr. 19, 2018

(30) Foreign Application Priority Data
Oct. 17, 2016 (JP) .................................. 2016-203357

(51) Int. Cl.
*G06T 11/00* (2006.01)
*A61B 6/00* (2006.01)
(Continued)

(52) U.S. Cl.
CPC .............. *G06T 11/005* (2013.01); *G06T 7/12* (2017.01); *G06T 7/149* (2017.01); *A61B 6/5205* (2013.01); *G06T 2207/20116* (2013.01)

(58) Field of Classification Search
CPC ......... G06T 11/005; G06T 7/12; G06T 7/149; G06T 2207/20116; A61B 6/5205
(Continued)

(56) References Cited

U.S. PATENT DOCUMENTS 8,194,946 B2 * 6/2012 Ida .......................... G06T 7/30
382/128
2001/0021264 A1 * 9/2001 Armato, III ............ G06T 7/66
382/132
(Continued)

FOREIGN PATENT DOCUMENTS

JP 2002-366961 A 12/2002
JP 2004-008419 A 1/2004
(Continued)

OTHER PUBLICATIONS

T.F. Cootes, et al. "Active Shape Models—Their Training and Application", Computer Vision and Image Understanding, vol. 61, No. 1, pp. 38-59. Jan. 1995.
(Continued)

*Primary Examiner* — Taeho Jo
(74) *Attorney, Agent, or Firm* — Canon U.S.A., Inc. IP Division

(57) ABSTRACT

A radiographing apparatus for identifying a contour of a predetermined target structure of a subject in an image, includes an area setting unit configured to set a contour search area where the contour is to be searched based on anatomical features of the structure of the subject, a contour candidate setting unit configured to set a contour candidate of the target structure, and a contour adjustment unit configured to adjust the contour candidate to approximate the contour candidate included in the contour search area to the contour of the target structure.

26 Claims, 12 Drawing Sheets

(51) Int. Cl.
*G06T 7/12* (2017.01)
*G06T 7/149* (2017.01)

(58) Field of Classification Search
USPC .................................................. 378/8
See application file for complete search history.

(56) References Cited

U.S. PATENT DOCUMENTS

| | | | | |
|---|---|---|---|---|
| 2002/0151793 | A1* | 10/2002 | Geiser | G06T 7/0012 600/450 |
| 2003/0228040 | A1* | 12/2003 | Oosawa | G06T 7/60 382/128 |
| 2004/0109595 | A1* | 6/2004 | Luo | G06T 7/149 382/132 |
| 2005/0169536 | A1* | 8/2005 | Accomazzi | G06T 7/149 382/228 |
| 2005/0207630 | A1* | 9/2005 | Chan | A61B 6/583 382/131 |
| 2005/0265606 | A1* | 12/2005 | Nakamura | G06T 7/0012 382/218 |
| 2007/0086640 | A1* | 4/2007 | Luo | G06T 7/149 382/132 |
| 2008/0260226 | A1* | 10/2008 | Moriya | G06K 9/6201 382/128 |
| 2010/0145231 | A1* | 6/2010 | Takahashi | G06T 7/0012 600/587 |
| 2011/0058720 | A1* | 3/2011 | Lu | G06T 7/12 382/131 |
| 2014/0009573 | A1* | 1/2014 | Fujita | G06T 7/0012 348/36 |
| 2015/0010219 | A1* | 1/2015 | Behiels | G06K 9/6232 382/128 |
| 2015/0043799 | A1* | 2/2015 | Zhan | G06K 9/3233 382/131 |
| 2015/0110245 | A1* | 4/2015 | Kim | A61B 6/488 378/62 |
| 2015/0119703 | A1* | 4/2015 | Mitchell | A61B 6/5294 600/425 |
| 2015/0265236 | A1* | 9/2015 | Garner | G06T 7/60 600/425 |
| 2016/0029992 | A1* | 2/2016 | Iijima | A61B 6/12 378/62 |
| 2016/0081663 | A1* | 3/2016 | Chen | A61B 8/0866 600/425 |
| 2017/0143993 | A1* | 5/2017 | Schmidt | G06F 16/51 |
| 2017/0259083 | A1* | 9/2017 | Nakatsugawa | A61N 5/1049 |
| 2018/0000439 | A1* | 1/2018 | Kawanabe | A61B 6/542 |

FOREIGN PATENT DOCUMENTS

| | | |
|---|---|---|
| JP | 2004-188202 A | 7/2004 |
| JP | 2014-064835 A | 4/2014 |
| JP | 2016-067832 A | 5/2016 |

OTHER PUBLICATIONS

Akinobu Shimizu; "Segmentation of Medical Images Using Deformable Models: A survey;" Medical Imaging Technology, vol. 20, No. 1, pp. 3-12.

* cited by examiner

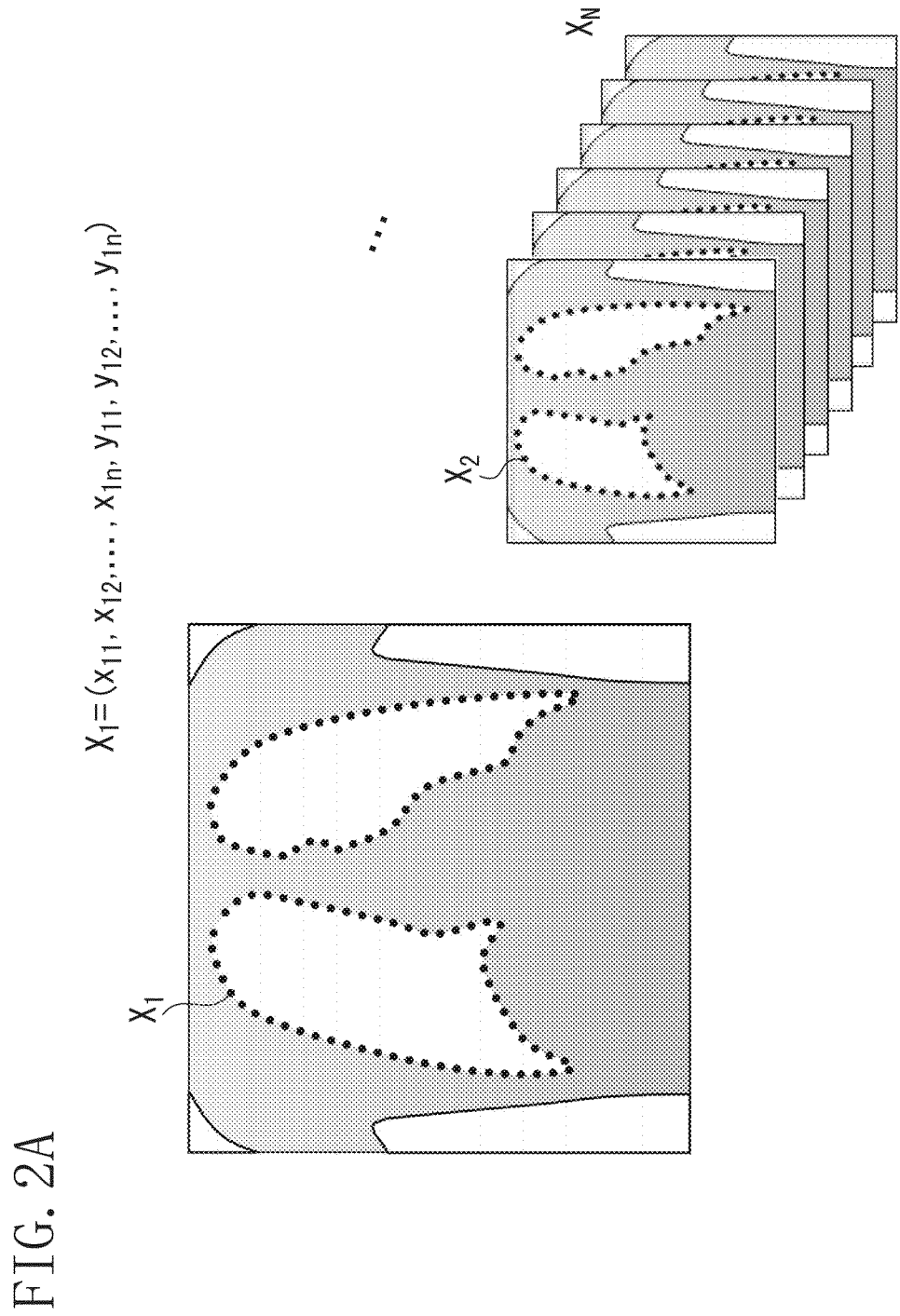

FIG. 2B
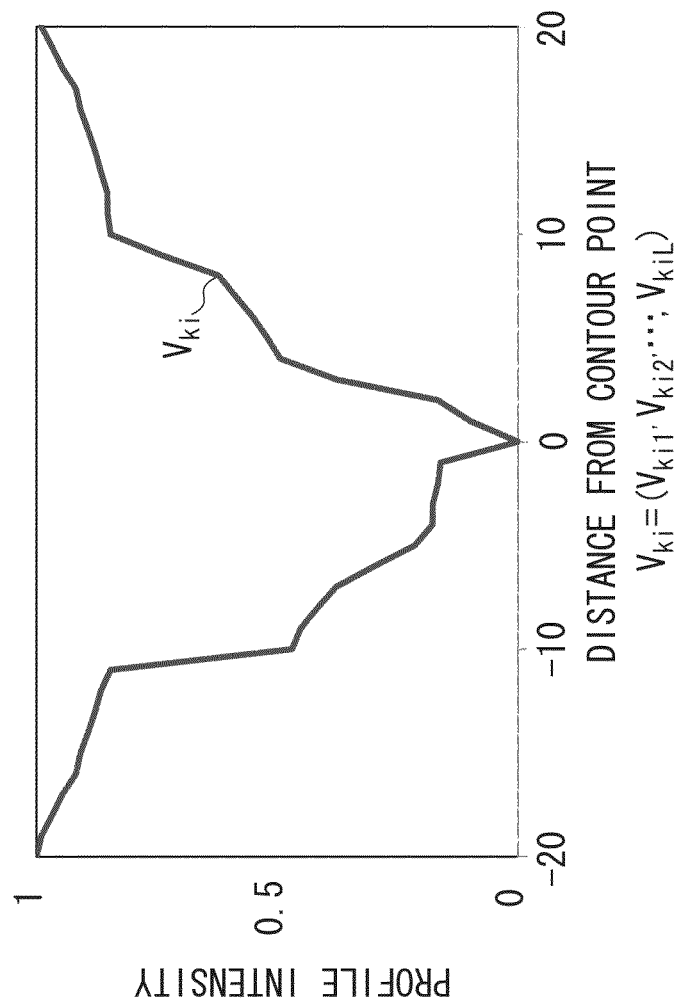
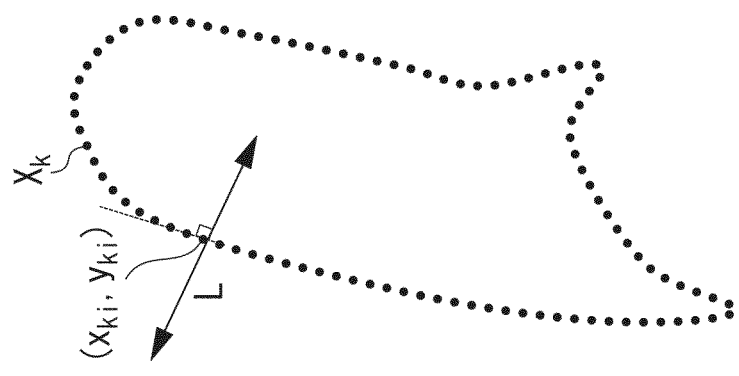

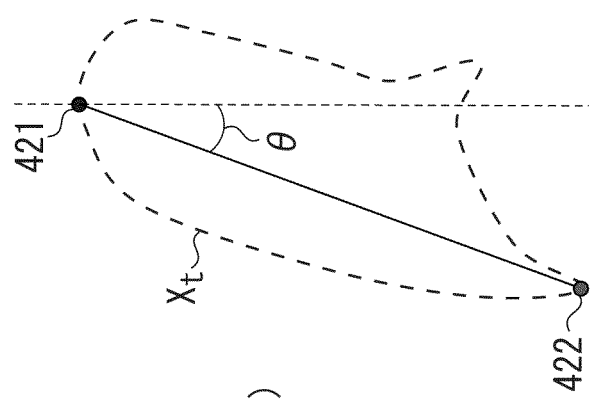
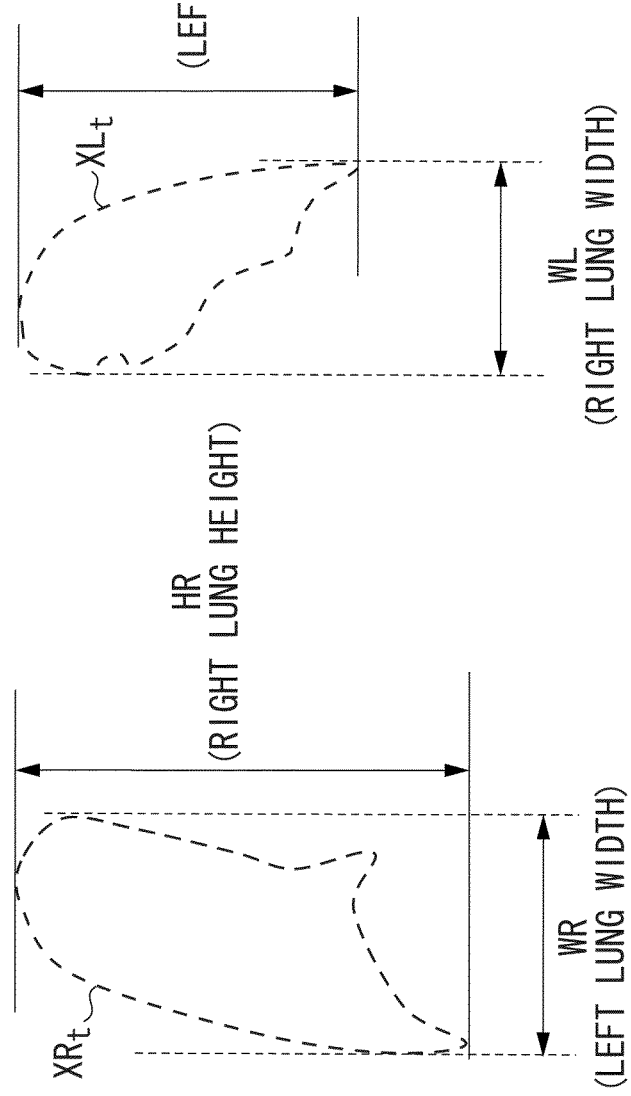
FIG. 6A
FIG. 6B

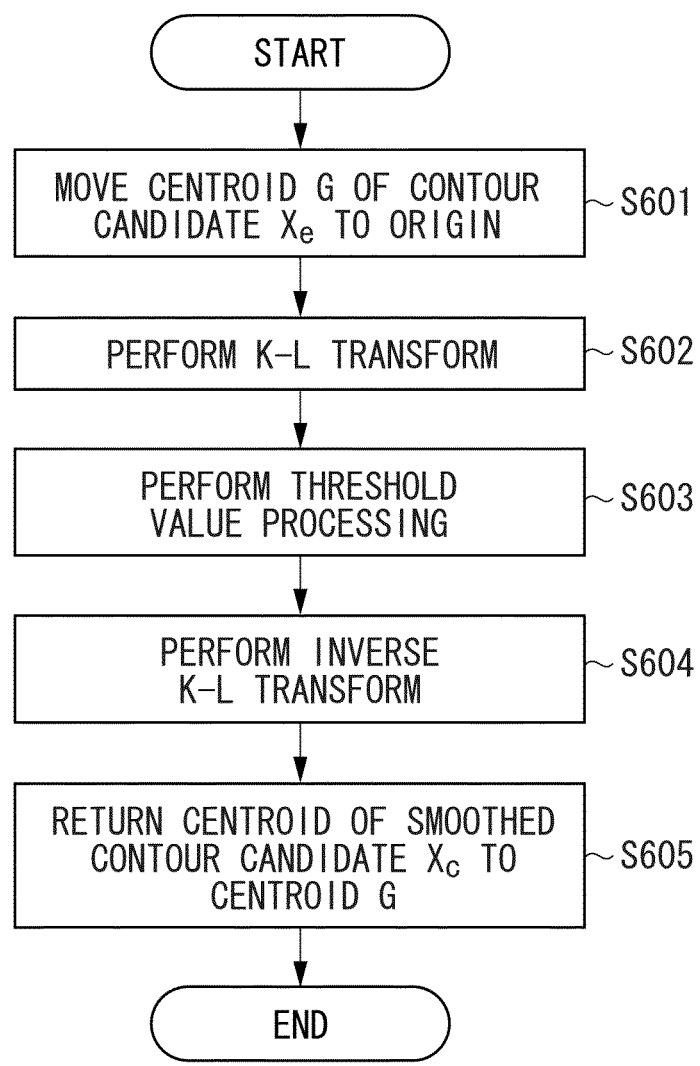

RADIOGRAPHING APPARATUS, RADIOGRAPHING SYSTEM, RADIOGRAPHING METHOD, AND STORAGE MEDIUM

BACKGROUND OF THE INVENTION

Field of the Invention

The present disclosure relates to a radiographing apparatus for identifying a contour of a predetermined target structure of a subject in an image, a radiographing system, a radiographing method, and a storage medium.

Description of the Related Art

In recent years, digital radiographing apparatuses have been widely used on medical fields. In various radiographing inspections and diagnoses, it is common to perform various types of image processing on an obtained digital image to produce many diagnostic values. In particular, a technique for automatically extracting the contour of a specific target structure from a subject in an image relates to many other image processing techniques, and has been an important technical issue.

As a typical example, there is proposed a technique for extracting the lung field contour from a front chest image obtained by using a radiographing apparatus, and automatically recognizing the shape and position of the lung field. The shape and position of the lung field in the front chest image are used for a wide range of diagnostic support applications, such as calculation of the cardiothoracic ratio (ratio of the heart width to the chest width) and automatic recognition of lung field knots. Therefore, high accuracy is required for contour extraction in these applications.

To meet this demand, a technique for automatically performing contour extraction of a predetermined structure from an image has been proposed. As a typical technique, an active shape model (T. F. Cootes et, al. "Active shape models", computer vision and image understanding vol. 61, no 1, January 1995) has been known. This technique performs statistical analysis of a plurality of sample images, and models the contour of a target structure as an extraction target through prior learning, and estimates the shape of the target structure based on the learned models. For example, Japanese Patent Application Laid-Open No. 2004-008419 proposes a technique for extracting the lung field contour by setting two different models, a shape model of the contour and a texture model representing local feature amounts (e.g., pixel values) around the contour, as contour-learned models.

However, the above-described conventional technique has the following problems in improving the contour extraction accuracy. The first problem is contour candidate erroneous detection in local search. In local search, a predetermined search range is set around contour candidates, and the most similar contour candidate is searched from the search range. If a target structure is not included in the set search range, an unsuitable contour candidate having a feature similar to the feature of the texture model may be erroneously extracted from the search range, possibly resulting in contour candidate erroneous detection. In particular, if a search range is set in an area largely shifted from an area where the contour of the desired target structure may exist, an unsuitable contour candidate may be extracted at a position largely shifted from the original contour in many cases.

The second problem is unsuitable deformation of a contour candidate when a contour shape feature is maintained. As described above, if an unsuitable contour candidate is included in some of contour candidates, making an attempt to maintain the contour shape feature may cause unsuitable deformation of contour candidates because contour candidate shapes are entirely affected by the unsuitable contour candidate.

If a local search and maintenance of contour shape feature are repeated in a state where these unsuitable contour candidates are extracted, search of the contour of the target structure will be repeated while being affected by the unsuitable contour candidates. As a result, the desired contour sometimes may not be extracted.

SUMMARY OF THE INVENTION

According to an aspect of the present disclosure, a radiographing apparatus for identifying a contour of a predetermined target structure of a subject in an image includes an area setting unit configured to set a contour search area where the contour is to be searched based on anatomical features of the structure of the subject, a contour candidate setting unit configured to set a contour candidate of the target structure, and a contour adjustment unit configured to adjust the contour candidate to approximate the contour candidate included in the contour search area to the contour of the target structure.

Further features of the present disclosure will become apparent from the following description of exemplary embodiments with reference to the attached drawings.

BRIEF DESCRIPTION OF THE DRAWINGS

FIG. 2A is a schematic diagram illustrating teacher data and a shape model in a learning circuit.

FIG. 2B is a schematic diagram illustrating a texture model in the learning circuit.

FIGS. 6A and 6B are diagrams respectively illustrating an example of adjusting a size of a contour candidate and an angle of the contour candidate based on anatomical features of a target structure.

FIG. 10 is a flowchart illustrating an example of a processing flow for smoothing a contour candidate.

DESCRIPTION OF THE EMBODIMENTS

Exemplary embodiments of the present disclosure will be described below with reference to the accompanying drawings. An example of a configuration of a radiographing system including a radiographing apparatus configured to identify the contour of a predetermined target structure of a subject in an image (e.g., a radiation image) will be described below with reference to FIG. 1.

Although in the present exemplary embodiment, an active shape model based on two models, a shape model of the contour and a texture model representing local feature amounts (such as pixel values) around the contour are used, other techniques for extracting the contour of a target structure are also applicable.

Figure 1A:
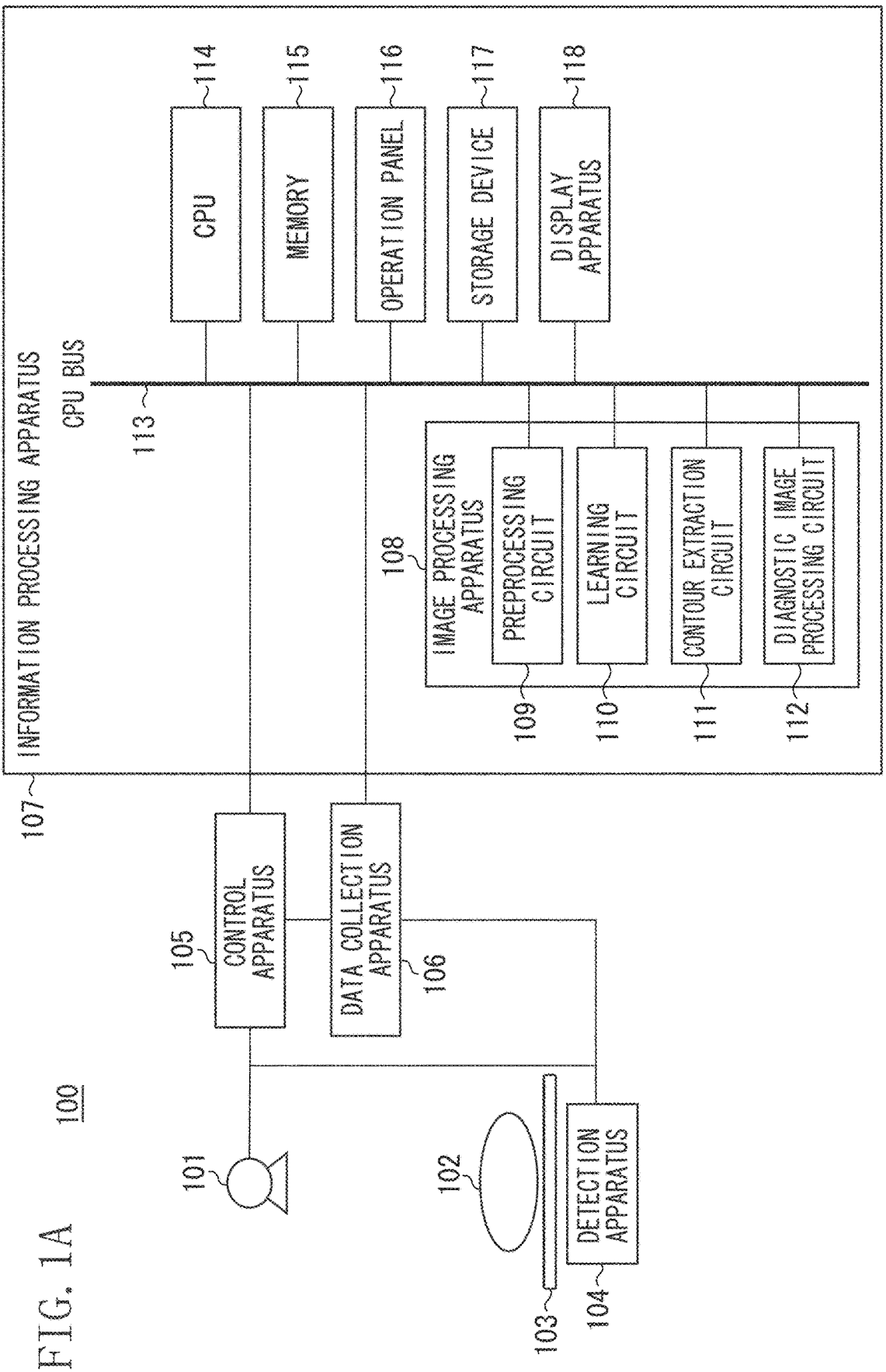
FIG. 1A is a block diagram illustrating an example of a basic configuration of a radiographing system including a radiographing apparatus according to an exemplary embodiment.
Figure 1B:
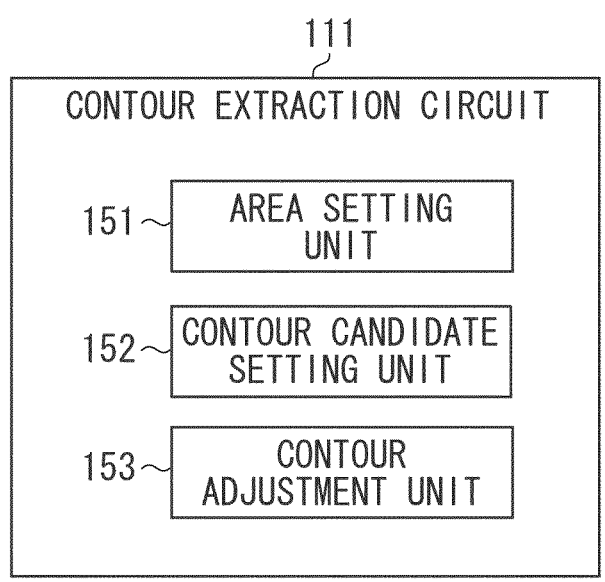
FIG. 1B is a block diagram illustrating an example of a basic configuration of a contour extraction circuit of the radiographing apparatus according to an exemplary embodiment.

FIG. 1A is a block diagram illustrating an example of a basic configuration of the radiographing system including the radiographing apparatus according to the present exemplary embodiment. FIG. 1B is a block diagram illustrating an example of a basic configuration of a contour extraction circuit of the radiographing apparatus according to the present exemplary embodiment.

A radiographing system 100 includes a radiation generating apparatus 101 for generating radiation, a bed 103 for positioning a subject 102, a radiation detection apparatus 104 for detecting radiation and outputting image data according to radiation that has transmitted through the subject 102, a control apparatus 105 for controlling a radiation generation timing and radiation generation conditions of the radiation generating apparatus 101, a data collection apparatus 106 for collecting various types of digital data, and an information processing apparatus (radiographing apparatus) 107 for performing image processing and entire apparatus control according to user instructions.

The information processing apparatus 107 includes an image processing apparatus 108 (including a preprocessing circuit 109, a learning circuit 110, a contour extraction circuit 111, and a diagnostic image processing circuit 112), a central processing unit (CPU) 114, a memory 115, an operation panel 116, a storage device 117, and a display apparatus 118, which are electrically connected with each other via a CPU bus 113.

The memory 115 stores various types of data required for processing by the CPU 114 and also includes a work memory for the CPU 114. The CPU 114 controls operations of the entire apparatus according to user instructions input to the operation panel 116 by using the memory 115.

The contour extraction circuit 111 includes an area setting unit 151, a contour candidate setting unit 152, and a contour adjustment unit 153.

According to the present exemplary embodiment, radiation refers to not only X-ray generally used but also alpha, beta, and gamma rays which are beams produced by particles (including photons) emitted by the radioactive decay, and other beams having similar or higher energy (for example, corpuscular beams and cosmic rays). An example in which an X-ray is used as a radiation beam will be described below.

The radiographing system 100 starts a sequence for capturing an image of the subject 102 according to a user instruction via the operation panel 116. The radiation generating apparatus 101 generates an X-ray having predetermined conditions, and the radiation detection apparatus 104 is irradiated with the X-ray that has transmitted through the subject 102. In this case, the control apparatus 105 controls X-ray generation conditions, such as voltage, current, and irradiation time, to enable the radiation generating apparatus 101 to generate X-ray under the predetermined conditions.

Image information output from the radiation detection apparatus 104 is converted into an electric signal by the radiation detection apparatus 104, and is collected as digital image data by the data collection apparatus 106. The image data collected by the data collection apparatus 106 is transferred to the information processing apparatus 107, and then is transferred to the memory 115 via the CPU bus 113 under control of the CPU 114. The image processing apparatus 108 applies various types of image processing to the image data stored in the memory 115. The image processing apparatus 108 generates an image suitable for extraction and diagnosis of the desired contour of the target structure, stores the result in the storage device 117, and displays the result on the display apparatus 118.

Detailed processing of the image processing apparatus 108 will be described below. The image processing apparatus 108 includes the preprocessing circuit 109, the learning circuit 110, the contour extraction circuit 111, and the diagnostic image processing circuit 112.

The preprocessing circuit 109 is provided with a circuit for performing preprocessing on image data. The preprocessing includes various types of correction processing for correcting characteristic variations resulting from the characteristics of the radiation detection apparatus 104 on the raw image data collected by the data collection apparatus 106, and suitably performing processing in subsequent stages.

The preprocessing circuit 109 selects suitable corrections according to the type of the radiation detection apparatus 104. Corrections includes dark correction, gain correction, defect correction, and logarithmic transform processing on image data. The dark correction is correction for eliminating fixed pattern noise of the radiation detection apparatus 104. The gain correction is correction for uniformalizing the sensitivity of the radiation detection apparatus 104 in the imaging plane. The defect correction is correction for interpolating defective pixels, included in the manufacturing process of the radiation detection apparatus 104, from surrounding pixels.

In response to the result of preprocessing and contour extraction processing (described below), the diagnostic image processing circuit 112 applies noise reduction processing, various types of enhancement processing, gradation conversion processing, and the like as diagnostic image processing, and performs other processing used for diagnosis.

An example in which the target structure is the lung field in a front chest image captured through plain X-ray imaging will be described below. However, the present exemplary embodiment is not limited to the lung field, and is also applicable to other target structures such as the heart.

In the present exemplary embodiment, an active shape model is used, and an initial position suitable as a contour candidate is set by using a shape model of the contour. Then, the local feature amount around the contour candidate is compared with the texture model, a more likely contour candidate is calculated, and the contour candidate at a more likely position is updated. Subsequently, deformation is performed on the updated contour candidate by using the shape model with the contour shape feature maintained. search processing by the above-described local search and maintenance of the contour shape feature is repeated to identify a final contour candidate.

The learning circuit 110 performs prior learning processing relating to the feature of the contour of the target structure. This processing is performed prior to X-ray imaging based on a number of pre-input learning images to generate a statistical model (learned model) of the feature representing the contour of the target structure. The type of the statistical model is not limited to particular types, and an optimal model is used depending on the type of the contour of the target structure.

The learning circuit 110 learns a shape model representing the statistical shape of the contour of the target structure. The learning circuit 110 learns the texture model representing the statistical local feature of the contour of the target structure by using a pixel value profile. According to the present exemplary embodiment, since the lung field in the front chest image is the target structure, the shape model based on the shape of the lung field contour and the texture model based on information about the pixel value profile around the lung field contour are applied.

First of all, the shape model of the contour of the lung field (target structure) will be described. As illustrated in FIG. 2A, teacher data in which the lung field contour of N learning images k (k=1 to N) is manually specified is prepared. The lung field contour is specified by using n contour points i (i=1 to n).

If the i-th contour point in the k-th learning image has the x-coordinate $x_{ki}$ and the y-coordinate $y_{ki}$, contour points are represented by a vector $X_k$ according to the formula (1). The number of contour points, n, and the number of learning images, N, are not limited to particular numbers. However, with the lung field contour in the front chest image, it is desirable, for example, to set n to 100 or a larger number and set N to 1500 or a larger number.

$$X_k = (x_{k1}, x_{k2}, \ldots, x_{kn}, y_{k1}, y_{k2}, \ldots, y_{kn}) \qquad (1)$$

Then, a vector of the contour points i is obtained for each of N learning images k. The obtained N vectors are represented by a matrix X according to the formula (2).

$$X = \begin{pmatrix} X_1 \\ X_2 \\ \vdots \\ X_N \end{pmatrix} = \begin{pmatrix} x_{11} & \cdots & x_{1n} & y_{11} & \cdots & y_{1n} \\ x_{21} & \cdots & x_{2n} & y_{21} & \cdots & y_{2n} \\ \vdots & \cdots & \vdots & \vdots & \cdots & \vdots \\ x_{N1} & \cdots & x_{Nn} & y_{N1} & \cdots & y_{Nn} \end{pmatrix} \qquad (2)$$

The matrix X is subjected to principal component analysis to be converted into X represented by formula (3), which is used as a shape model X of the lung field contour.

$$X = X_{mean} + P_S \cdot b_S \qquad (3)$$

$X_{mean}$ denotes the average shape of X, $P_S$ denotes the main component vector, and $b_S$ denotes the eigen value. The main component to be used is freely selectable. For example, it is desirable to select the main component vector so as to achieve a cumulative contribution rate of 90%.

Next, the texture model of the lung field contour will be described. As illustrated in FIG. 2B, for each contour point i of the lung field, a pixel value profile $v_{im}$ is obtained in the perpendicular direction of the profile line. When the profile length is L (m=1 to L), if the pixel value profile $v_{im}$ in the k-th learning image is calculated for each contour point, a pixel value profile $v_{kim}$ (i=1 to n, m=1 to L) is represented by a matrix $V_k$ according to formula (4).

When a pixel value profile is obtained, it is desirable to normalize an image signal. For example, when each pixel value profile $v_{im}$ is converted into 0 to 1 based on the maximum and minimum values of the obtained pixel value profiles, the image signal is normalized. The image signal may also be normalized by normalizing all of the learning images to 0 to 1 and then obtaining the pixel value profile $v_{im}$. It is desirable to set the profile length L, for example, to 40 pixels or more.

$$V_k = \begin{pmatrix} v_{k11} & v_{k12} & \cdots & v_{k1L} \\ v_{k21} & v_{k22} & \cdots & v_{k2L} \\ \vdots & \vdots & \cdots & \vdots \\ v_{kn1} & v_{kn2} & \cdots & v_{knL} \end{pmatrix} \qquad (4)$$

Similar to the shape model, the pixel value profile $V_k$ represented by formula (4) is obtained for each of N learning images. Then, the matrix $V_k$ is subjected to principal component analysis to be converted into V represented by formula (5), which is used as a texture model V of the lung field contour.

$$V = V_{mean} + P_A \cdot b_A \qquad (5)$$

$V_{mean}$ denotes the average shape of V, $P_A$ denotes the main component vector, and $b_A$ denotes the eigen value. The main component to be used is freely selectable. For example, it is desirable to select the main component vector so as to achieve a cumulative contribution rate of 90%.

As described above, recalculated models may be stored in the storage device 117 as general-purpose models for the radiographing apparatus 104, and used as shape and texture models. The shape and texture models may be calculated according to use conditions of the radiographing apparatus 104 on the assumption that the image data captured by each radiographing apparatus 104 is used as the learning images k.

The contour extraction circuit 111 performs processing for identifying (or extracting) the contour of a predetermined target structure from the subject 102. The processing flow of the contour extraction circuit 111 will be described below with reference to FIG. 3.

In step S301, the contour extraction circuit 111 performs analysis preparation processing on a preprocessed image obtained by the preprocessing circuit 109. The analysis preparation processing aims for improving the contour extraction accuracy in processing in subsequent stages. The contour extraction circuit 111 selects processing suitable for the target structure. The analysis preparation processing includes image signal normalization processing, edge enhancement processing for enhancing the contour to be extracted, gradation conversion processing, noise reduction processing, and rotation processing for making the direction of the calculation target image the same. The analysis preparation processing further includes enlargement/reduction processing for normalizing the on-image subject size in a case of a different pixel size of the radiation detection apparatus 104.

In step S302, the contour extraction circuit 111 sets a first contour candidate $X_t$. The contour candidate setting unit 152 sets a contour candidate of the target structure. The contour candidate $X_t$ includes n contour points which is the same number of contour points as the shape model generated by the learning circuit 110. The contour candidate $X_t$ is represented by a vector according to formula (6).

$$X_t = (x_{t1}, x_{t2}, \ldots, x_{tn}, y_{t1}, y_{t2}, \ldots, y_{tn}) \qquad (6)$$

The first contour candidate $X_t$ serves as the initial position at the time of successive contour search for the contour by contour search loop processing in steps S303 to S308. An arbitrary position may be set as the contour candidate $X_t$. The contour extraction accuracy increases if the contour candidate $X_t$ is set as the initial position at a position as close to the desired contour of the target structure as possible. Therefore, it is desirable, for example, to set as the initial position the average shape $X_{mean}$ of the lung field obtained at the time of the learning of the shape model. In this way, the contour candidate setting unit 152 sets the initial position of the contour candidate based on the shape model.

In steps S303 to S305, the contour extraction circuit 111 preforms processing of calculating and estimating local feature amounts characterizing the contour of the lung field (target structure) from a predetermined search range (contour search area), and performs contour search processing. In step S303, based on the local feature amount of the contour candidate of the lung field (target structure), the contour extraction circuit 111 sets a contour search area S where the lung field contour is to be searched. More specifically, based on anatomical features of the structure of the subject 102, the area setting unit 151 sets the contour search area S where the contour of the target structure is to be searched.

Figure 4:
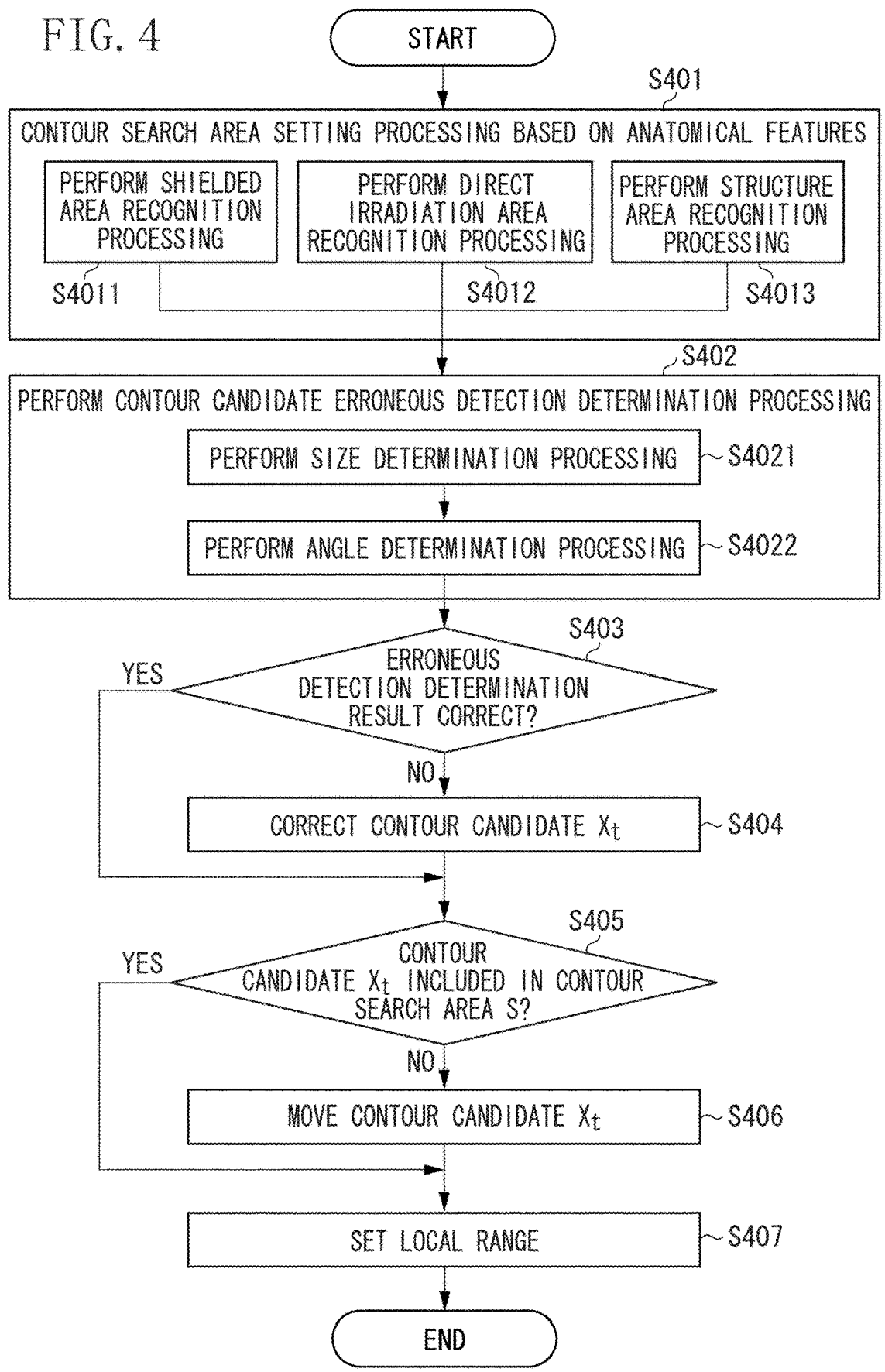
FIG. 4 is a flowchart illustrating an example of a processing flow for setting a contour search area, correcting a contour candidate, and setting a local area.

FIG. 4 is a flowchart illustrating detailed processing in step S303. The processing in step S303 will be described in detail below with reference to FIG. 4.

In step S401, the contour extraction circuit 111 performs processing of calculating the anatomical features of the subject 102. This processing is performed independently of the statistical model (learned model) obtained by the learning circuit 110 aiming for calculating the contour search area S where the contour of the target structure is likely to exist based on the anatomical features of the subject 102. The area setting unit 151 sets the contour search area S based on at least one of a structure area indicating the anatomical features of the structure of the subject 102, a shielded area which is shielded from radiation, and a direct irradiation area where the radiation detection apparatus 104 is directly irradiated with radiation.

Figure 5:
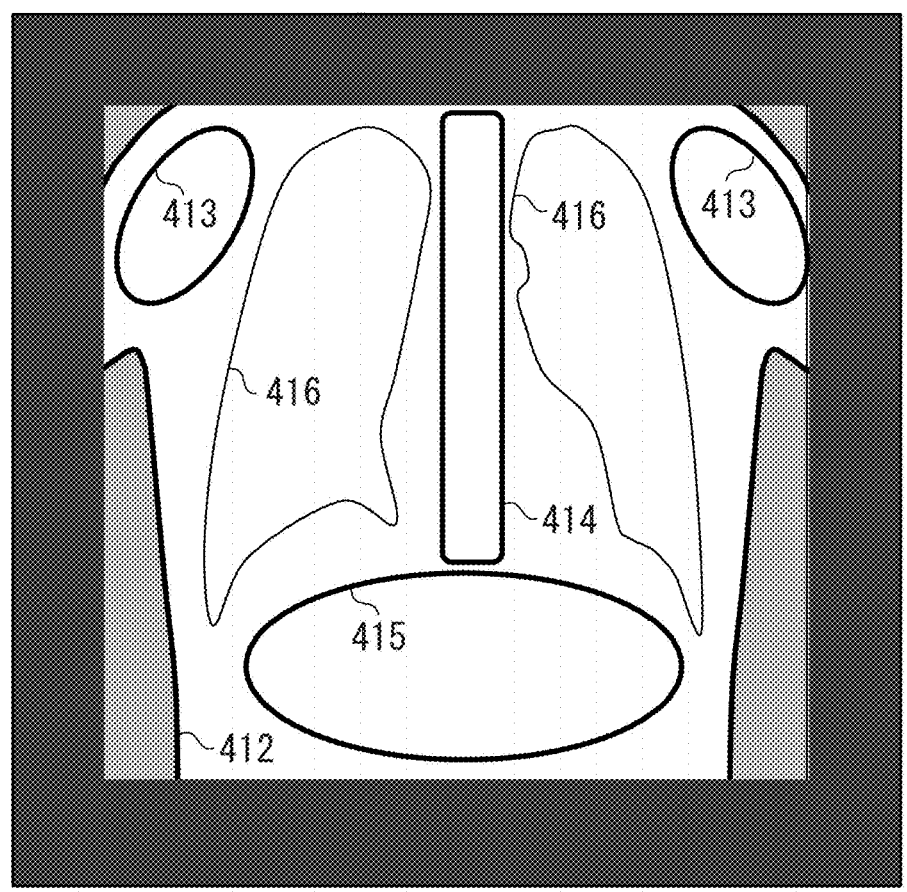
FIG. 5 illustrates an example of a front chest image including a structure area, a shielded area, and a direct irradiation area.

Now, the anatomical features of the subject 102 will be described based on the front chest image illustrated in FIG. 5 as a specific example. The front chest image is roughly divided into six areas: a shielded area 411, a direct irradiation area 412, a shoulder joint and arm area 413 (first structure area), a backbone area (second structure area) 414, an abdomen area (third structure area) 415, and a lung field area (fourth structure area) 416.

The shielded area 411 is an area shielded from radiation by a collimator. The irradiation area 412 is an area where the radiation detection apparatus 104 is directly irradiated with radiation that does not transmit through the subject 102. The shoulder joint and arm area 413 is an area which includes anatomical features of the shoulder joints and arms of the subject 102. The backbone area 414 is an area which includes anatomical features of the backbone of the subject 102. The abdomen area 415 is an area which includes anatomical features of the abdomen of the subject 102. The lung field area 416 is an area which includes anatomical features of the lung field of the subject 102.

This processing includes shielded area recognition processing for recognizing the shielded area 411 (step S4011), direct irradiation area recognition processing for recognizing the irradiation area 412 (step S4012), and structure area recognition processing for recognizing the structure areas (the shoulder joint and arm area 413, the backbone area 414, and the abdomen area 415) of the subject 102 (step S4013).

According to the present exemplary embodiment, the contour extraction circuit 111 excludes the areas 411 to 415 recognized in steps S4011 to S4013 from the image data of the subject 102, estimates the lung field area 416, and sets the lung field area 416 as the contour search area S. In this way, based on anatomical features of a structure other than the target structure, the area setting unit 151 may identify the structure areas 413, 414, and 415 of a structure other than the lung field (target structure) and may set the contour search area S from areas other than the structure areas 413, 414, and 415.

A known technique is applicable to the processing for recognizing a structure area based on the anatomical features of the subject 102. All of the recognition processing in steps S4011 to S4013 may be used, or recognition processing may be selected according to the target structure.

In step S402, the contour extraction circuit 111 performs erroneous detection determination processing on the contour candidate $X_t$. This processing aims for determining whether the contour candidate $X_t$ set in step S302 or S308 has a structure suitable as the lung field (target structure) based on the anatomical features of the subject 102. In step S403, the contour extraction circuit 111 confirms the result of the erroneous detection determination processing. When the result of the erroneous detection determination processing is incorrect (NO in step S403), the processing proceeds to step S404. In step S404, the contour extraction circuit 111 corrects the contour candidate $X_t$. On the other hand, when the result of the erroneous detection determination processing is correct (YES in step S403), the processing proceeds to step S405.

Suitable examples of the erroneous detection determination processing for the contour candidate $X_t$ include determination processing based on the size and angle of the contour candidate $X_t$. Size determination processing (step S4021) based on the size of the contour candidate $X_t$ and angle determination processing (step S4022) based on the angle of the contour candidate $X_t$ will be described below.

In the size determination processing in step S4021, the contour extraction circuit 111 calculates the size of the lung field defined by the contour candidate $X_t$. As illustrated in FIG. 6A, based on a right lung contour candidate $XR_t=(xr_{t1}, xr_{t2}, \ldots, xr_{tm}, yr_{t1}, yr_{t2}, \ldots, yr_{tm})$ and a left lung contour candidate $XL_t=(xl_{t1}, xl_{t2}, \ldots, xl_{tm}, yl_{t1}, yl_{t2}, \ldots, yl_{tm})$, the contour extraction circuit 111 obtains a left lung height HL, a right lung height HR, a left lung width WL, and a right lung width WR according to formula (7).

$$WR = \max(xr_{t1}, xr_{t2}, \ldots, xr_{tm}) - \min(xr_{t1}, xr_{t2}, \ldots, xr_{tm})$$

$$WL = \max(xl_{t1}, xl_{t2}, \ldots, xl_{tm}) - \min(xl_{t1}, xl_{t2}, \ldots, xl_{tm})$$

$$HR = \max(yr_{t1}, yr_{t2}, \ldots, yr_{tm}) - \min(yr_{t1}, yr_{t2}, \ldots, yr_{tm})$$

$$HL = \max(yl_{t1}, yl_{t2}, \ldots, yl_{tm}) - \min(yl_{t1}, yl_{t2}, \ldots, yl_{tm}) \quad (7)$$

For the right and left lung heights HR and HL, the right and left lung widths WR and WL, the right-to-left ratio of the lung heights, and the right-to-left ratio of the lung widths, the contour extraction circuit 111 totals a plurality of pieces of clinical data, and sets clinical data variation ranges relating to the right and left lung heights, the right and left lung widths, the right-to-left ratio of the lung heights, and the right-to-left ratio of the lung widths.

Based on the information about the variation ranges, the contour extraction circuit 111 determines whether the size of the lung field estimated from the contour candidate $X_t$ is out of the variation range. When the size of the lung field is out of the variation range (NO in step S405), then in step S404, the contour extraction circuit 111 performs processing for enlarging or reducing the contour candidate $X_t$ so that the lung field size falls within the variation range.

In the lung field angle recognition processing in step S4022, the contour extraction circuit 111 calculates the positional angle θ of the lung field based on the right lung contour candidate $XR_t$ and the left lung contour candidate $XL_t$. In this processing, as illustrated in FIG. 6B, the contour extraction circuit 111 recognizes a lung apex 421 and a costotransverse angle 422 as anatomical features of the lung field through image processing, and calculates the angle θ formed between the Y axis and the straight line connecting the lung apex 421 and the costotransverse angle 422. Similar to step S4021, for the angle θ, the contour extraction circuit 111 totals a plurality of pieces of clinical data in advance, and sets a clinical data variation range relating to the positional angle of the lung field.

Based on information about the variation range, the contour extraction circuit 111 determines whether the positional angle of the lung field estimated from the contour candidate $X_t$ is out of the variation range. When the positional angle of the lung field is out of the variation range (NO in step S403), then in step S404, the contour extraction circuit 111 performs processing for rotating the contour candidate $X_t$ so that the positional angle of the lung field falls within the variation range.

In this way, the contour adjustment unit 153 adjusts at least one of the size, angle, and position of the contour candidate $X_t$ based on the anatomical features of the target structure. In the case of a deviation from anatomical features (size, angle, position, etc.) of the target structure based on the variation range estimated as the target structure of the human body, correcting the contour candidate $X_t$ through the above-described processing enables starting searching for the contour of the target structure from a more correct position. As a result, the extraction accuracy for the final contour candidate can be improved.

In step S405, the contour extraction circuit 111 determines whether the contour candidate $X_t$ is included in the contour search area S calculated in step S401. When the contour candidate $X_t$ is not included in the contour search area S (NO in step S405), the processing proceeds to step S406.

In step S406, the contour extraction circuit 111 performs processing for moving the contour points of the contour candidate $X_t$ that is not included in the contour candidate area S to the inside of the contour candidate area S. When at least a part of the contour candidate $X_t$ is not included in the contour search area S, the contour adjustment unit 153 moves the contour candidate $X_t$ so that the contour candidate $X_t$ is included in the contour search area S.

Figure 7:
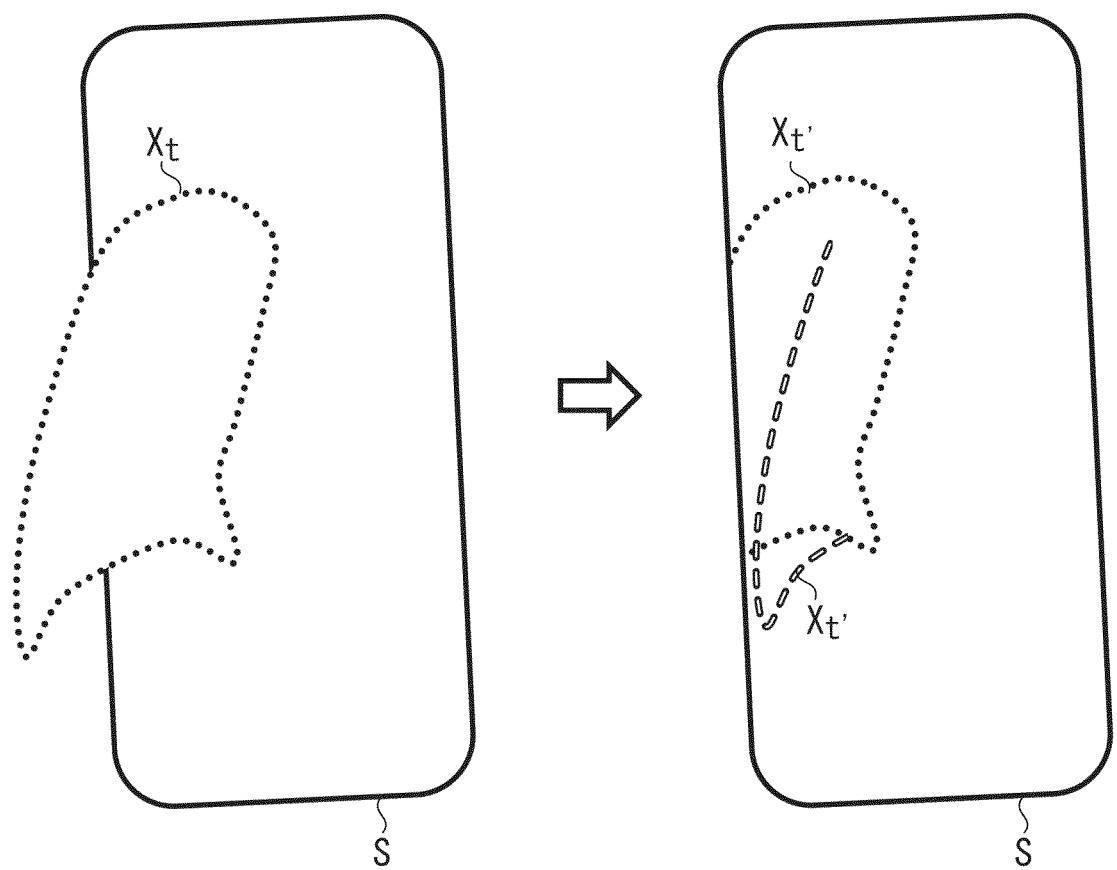
FIG. 7 is a diagram illustrating an example of separating a part of a contour candidate from the contour candidate and then moving the part.
Figure 8:
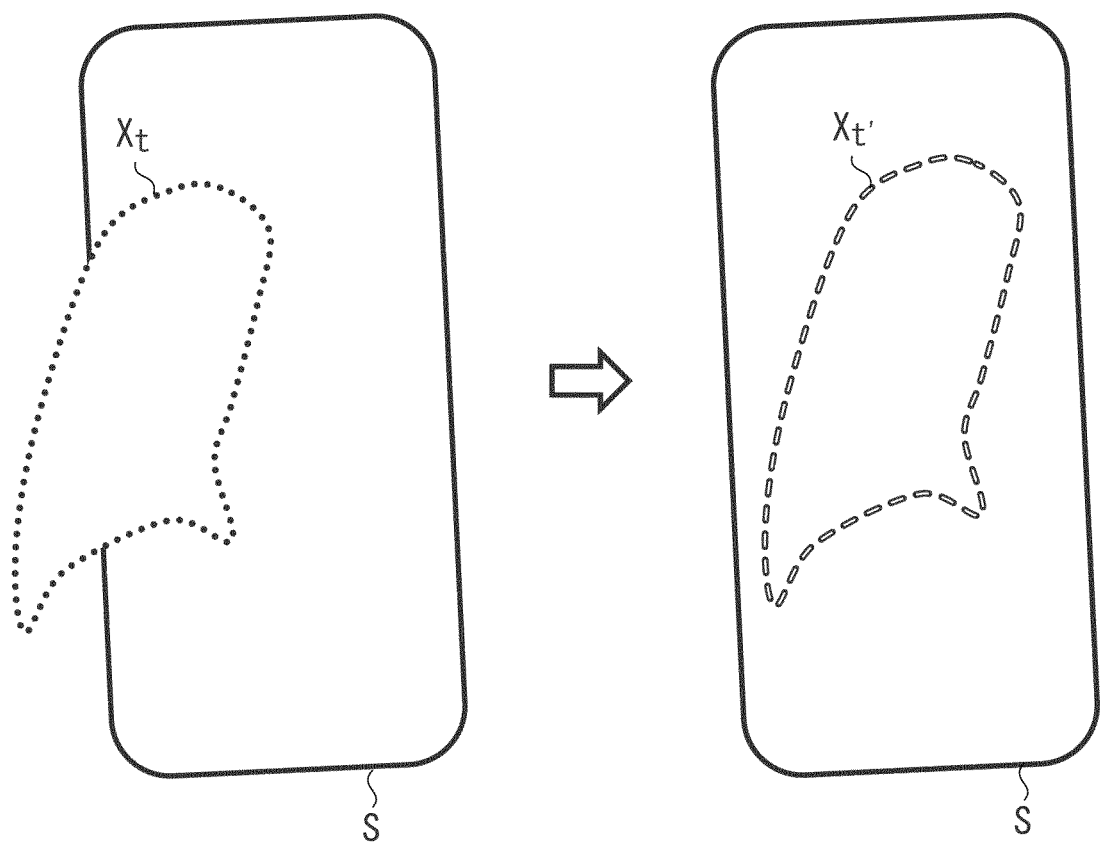
FIG. 8 is a diagram illustrating an example of moving the entire contour candidate.

For example, as illustrated in FIG. 7, the contour adjustment unit 153 translates the contour points of the contour candidate $X_t$ that is not included in the contour search area S to the inside of the contour candidate area S, and updates the contour candidate $X_t$ to an updated contour candidate $X_t'$. In this way, the contour adjustment unit 153 separates from the contour candidate $X_t$ a part of the contour candidate $X_t$ which is not included or of which the peripheral region is not included in the contour search area S, and then moves the part. As illustrated in FIG. 8, the contour adjustment unit 153 may translate all of the contour points of the contour candidate $X_t$ to the inside of the contour candidate area S so that the contour points of the contour candidate $X_t$ are included in the contour candidate area S, and updates the contour candidate $X_t$ to the updated contour candidate $X_t'$.

When at least a part of a predetermined peripheral region of the contour candidate $X_t$ (e.g., a local area where the local feature amount of the contour is extracted) is not included in the contour search area S, the contour adjustment unit 153 may move the contour candidate $X_t$ so that the peripheral region is included in the contour search area S.

When the contour candidate $X_t$ is included in the contour search area S (YES in step S405), the processing proceeds to step S407.

In step S407, to acquire the local feature amount (e.g., pixel values) around the contour candidate $X_t$, the contour extraction circuit 111 sets a local range (local area) D of each contour point. For each contour point of the contour candidates $X_t$ and $X_t'$, the contour extraction circuit 111 sets a profile length $L_s$ in the perpendicular direction of the profile line, and sets the range of the profile length $L_s$ included in the contour search area S as the local range D for each contour point. Although there is no limitation on the profile length $L_s$, it is desirable, for example, in lung field contour extraction, to set the profile length $L_s$ to a value about twice the pixel value profile length L of the texture model.

Figure 3:
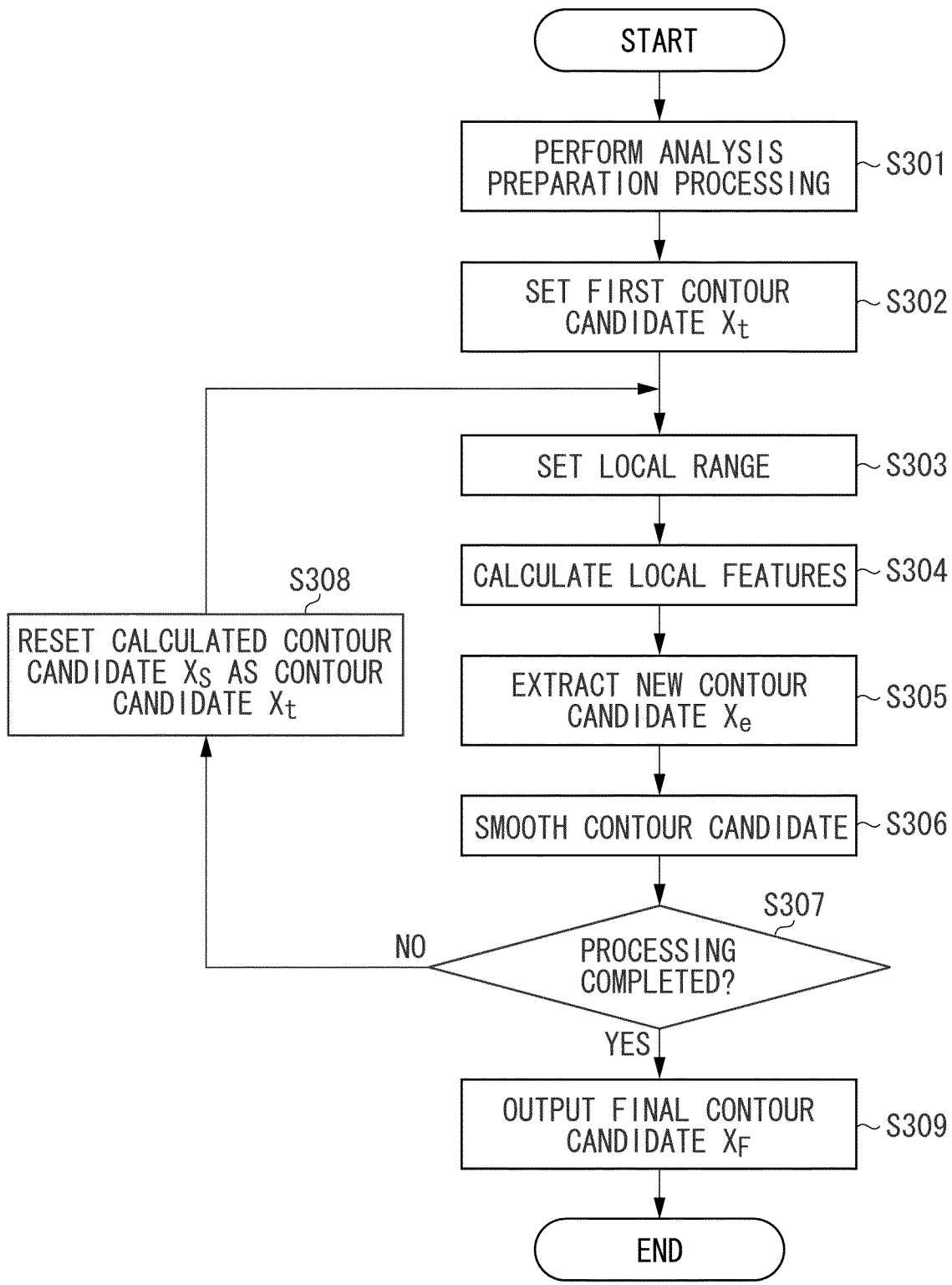
FIG. 3 is a flowchart illustrating an example of a processing flow of a contour extraction circuit.
Figure 9A:
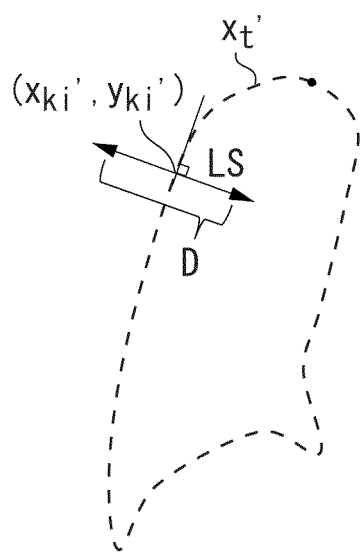
FIGS. 9A and 9B are diagrams respectively illustrating an example of a local area of a contour candidate and an example of selecting a new contour point in the local area of the contour candidate.
Figure 9B:
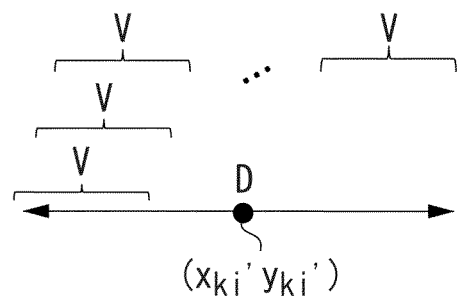

In step S304 illustrated in FIG. 3, the contour extraction circuit 111 performs processing of calculating local features of the contour candidates $X_t$ and $X_t'$ in the local range D set in step S303. The information about the pixel value profile is used as local features. FIGS. 9A and 9B illustrate the local range D of the pixel value profile of the updated contour candidate $X_t'$. As illustrated in FIG. 9A, the contour extraction circuit 111 sets the local range D of the profile length $L_s$ (number of profiles, $L_s$) in the perpendicular direction of the profile line centering on a contour point ($x_{ki}'$, $y_{ki}'$), and calculates the pixel value profile in the local range D for each contour point. As a result, a pixel value profile of the contour candidate $X_t'$ (the number of contour points n, multiplied by the number of profiles $L_s$) is obtained.

In step S305, for each contour point of the contour candidate $X_t'$, the contour extraction circuit 111 extracts a new contour candidate $X_e$ from each obtained pixel value profile. As illustrated in FIG. 9B, the contour extraction circuit 111 calculates the contour candidate $X_e$ by comparing the pixel value profile in the local range D of each contour point with the pixel value profile v of the texture model and then selecting a mutually similar point as a new contour point.

The contour adjustment unit 153 adjusts the contour candidate by comparing the local feature (image profile v) of the contour of the target structure of the texture model with the local feature of the contour candidate $X_t'$. The contour adjustment unit 153 adjusts the contour candidate to the position (contour candidate $X_e$) which provides the highest similarity between the local feature (image profile v) of the contour of the target structure of the texture model and the local feature of the contour candidate $X_t'$. In this way, the contour adjustment unit 153 adjusts the contour candidate to approximate the contour candidate $X_t'$ included in the contour search area S to the contour of the target structure.

The method for searching for a similar point is not limited specifically. For example, according to formula (8), it is desirable to perform the K-L transform on a pixel value profile g(m) in the local range D of a predetermined contour point by using the average shape $V_{mean}$ and the main component vector $P_A$ of the corresponding contour point of the texture model, and then select as a new contour point a contour point i where the distance between the pixel value profile in the local range D and the pixel value profile of the texture model is minimized.

$$i = \min_{m} \|P_A^T * (g(m) - V_{mean})\| \quad (8)$$

$$(m = 1, 2, \ldots, L_s)$$

In step S306, the contour extraction circuit 111 performs smoothing processing on the contour candidate $X_e$. As a new contour candidate $X_e$, the contour extraction circuit 111 selects a contour point which is most similar to the texture model of the pixel value profile of the lung field contour. However, when there is a comparatively small number of times of the contour search loop in steps S303 to S308 and there is a large difference between the contour candidate $X_e$ and the actual contour, the shape of the contour candidate $X_e$ may largely collapse from a shape suitable as the lung field (target structure). Then, the smoothing processing means processing for forming the contour candidate $X_e$ to a shape suitable as the lung field. A known technique is applicable to the smoothing processing. As a suitable example, the processing in the flowchart illustrated in FIG. 10 will be described below.

In step S601, according to formula (9), the contour extraction circuit 111 performs coordinate conversion for moving the centroid G=(Gx, Gy) of the contour candidate $X_e$ to the origin (0, 0) and then calculate a contour shape $X_e'$. The contour extraction circuit 111 performs processing in steps S602 to S604 on the shape of the contour in a state where the on-image position information of the contour shape is excluded.

$$\begin{cases} X_e' = X_e - G = (x_{e1} - Gx, \ldots, x_{en} - Gx, y_{e1} - Gy, \ldots, y_{en} - Gy) \\ X_e = (x_{e1}, x_{e2}, \ldots, x_{en}, y_{e1}, y_{e2}, \ldots, y_{en}) \\ G = (Gx, Gy) = \left(\frac{x_{e1} + x_{e2} + \ldots + x_{en}}{n}, \frac{y_{e1} + y_{e2} + \ldots + y_{en}}{n}\right) \end{cases} \quad (9)$$

In step S602, according to formula (10), the contour extraction circuit 111 performs the K-L transform using the average shape $X_{mean}$ and the main component vector $P_S$ in the shape model to obtain a contour shape c in the conversion coordinate system.

$$C = P_S^T \cdot (X_e' - X_{mean}) \quad (10)$$

In step S603, according to formula (11), the contour extraction circuit 111 performs threshold value processing on the contour shape c in the conversion coordinate system using the eigen value $b_S$ and an arbitrary coefficient m of the shape model to calculate a contour shape c' in the conversion coordinate system. The coefficients m is an arbitrary coefficient for determining the smoothness, and is set to, for example, around 3. j denotes the number of vectors when the main component vector is selected so as to achieve a cumulative contribution rate of 90% when a shape model of the lung field (target structure) is generated.

$$\begin{cases} c_i' = c_i \left(-m\sqrt{\lambda_i} < c_i < m\sqrt{\lambda_i}\right) \\ c_i' = -m\sqrt{\lambda_i} \left(c_i \leq -m\sqrt{\lambda_i}\right), c = \begin{pmatrix} c_1 \\ \vdots \\ c_i \\ \vdots \\ c_j \end{pmatrix}, bs = \begin{pmatrix} \lambda_1 \\ \vdots \\ \lambda_i \\ \vdots \\ \lambda_j \end{pmatrix} \\ c_i' = m\sqrt{\lambda_i} \left(c_i \geq m\sqrt{\lambda_i}\right) \end{cases} \quad (11)$$

$(i = 1, 2, \ldots, j)$

In step S604, the contour extraction circuit 111 performs the inverse K-L transform on the contour shape c' having undergone the threshold value processing in the conversion coordinate system, according to formula (12), and calculates a smoothed contour candidate $X_c$.

$$X_c = X_{mean} + P_S \cdot c' \quad (12)$$

In step S605, according to formula (13), the contour extraction circuit 111 moves the centroid of the contour candidate $X_c$ (origin) to the centroid G=(Gx, Gy) before coordinates conversion, and calculates a smoothed contour candidate $X_S$.

$$X_S = X_c + G \quad (13)$$

In this way, the contour adjustment unit 153 smoothes the contour candidate based on the shape model. The above-described processing enables integrating the contour candidate with the shape model and updating the contour candidate to the contour candidate $X_S$ while ensuring a shape suitable as the lung field.

In step S307 illustrated in FIG. 3, the contour extraction circuit 111 determines whether to end the contour search loop processing according to whether the contour search loop processing has been repeated a predetermined number of times. When the contour search loop processing has been repeated the predetermined number of times (YES in step S307), the contour extraction circuit 111 ends the contour search loop processing.

To avoid performing the contour search loop processing more than necessary to shorten the processing time, the contour extraction circuit 111 may calculate the difference between a contour candidate $X_{S1}$ calculated in the previous contour search loop and a contour candidate $X_{S2}$ calculated in the current contour search loop, and determine whether the difference is equal to or smaller than a predetermined threshold value. When the difference is equal to or smaller than the predetermined threshold value, the contour extraction circuit 111 determines that the updated contour candidate $X_S$ is close to the actual contour, and ends the contour search loop processing.

Further, the contour extraction circuit 111 may determine to end the contour search loop processing by combining the determination by the number of times of the contour search loop and the determination by the difference between the contour candidates. When the contour extraction circuit 111 determines to continue the contour search loop processing (NO in step S307), the processing proceeds to step S308. On the other hand, when the contour extraction circuit 111 determines to end the contour search loop processing (YES in step S307), the processing proceeds to step S309.

In step S308, to continue the contour search loop processing, the contour extraction circuit 111 resets the contour candidate $X_S$ calculated in step S306 as the contour candidate $X_t$, and the processing returns to step S303. Then, the contour extraction circuit 111 continues the contour search loop processing. In this case, the contour candidate setting unit 152 resets the adjusted contour candidate $X_S$ as the updated contour candidate $X_t$. In step S303 to S306, to approximate the updated contour candidate $X_t$ to the contour of the target structure, the contour adjustment unit 153 readjusts the contour candidate.

In step S309, the contour extraction circuit 111 ends the contour search loop processing, and outputs the contour candidate $X_S$ as a final contour candidate $X_F$.

Through the above-described processing, the contour extraction circuit 111 can implement the function of extracting the contour of a predetermined target structure from the subject 102.

To improve the accuracy of the extraction result, the contour extraction circuit 111 may perform processing in steps S301 to S309 with a plurality of resolutions. In this case, the contour candidate setting unit 152 resets the contour candidate $X_S$ adjusted in the image having a first resolution (radiation image) as the updated contour candidate $X_t$ in the image having a second resolution different from the first resolution. Then, to approximate the updated contour candidate $X_t$ to the contour of the target structure, the contour adjustment unit 153 readjusts the contour candidate in the image having the second resolution (radiation image).

In this case, it is desirable that the second resolution is higher than the first resolution. The contour extraction accuracy can be improved by sequentially performing the contour search processing with increasing resolution, more specifically, by updating the contour candidate $X_F$ with a lower resolution to the first contour candidate $X_t$ with a higher resolution in the subsequent stage.

In image data contour extraction, the radiographing apparatus according to the present exemplary embodiment sets the contour search area S by using anatomical features of the target structure, corrects the size, angle, and position of the contour candidate, and moves the contour candidate so that the contour candidate is included in the contour search area S. As a result, it becomes possible to suitably manage a local feature search range, and accordingly extract a suitable contour candidate. Even if an unsuitable contour point deviated from the contour of the target structure is extracted, correcting the position of the unsuitable contour point enables correcting the influence of the unsuitable contour point and correctly extracting a desired contour.

While the disclosure has specifically been described based on a preferred exemplary embodiment, the present invention is not limited thereto, naturally, and can be modified in diverse ways within the ambit of the appended claims. As suitable examples of operations of the learning circuit 110 and the contour extraction circuit 111 according to the present exemplary embodiment, in particular, the lung field contour in a front chest image captured through plain X-ray imaging is recognized as the contour of the target structure, applications of the present disclosure are not limited thereto. For example, the disclosure is applicable not only to X-ray images but also to CT images and images captured by ordinary cameras.

The above-described features may also be applied in a configuration in which software (program) for implementing the functions of the above-described exemplary embodiment is directly or remotely read by a computer of a system or apparatus and the program code is executed by the computer.

Embodiments of the present disclosure can also be realized by a computer of a system or apparatus that reads out and executes computer executable instructions recorded on a storage medium (e.g., non-transitory computer-readable storage medium) to perform the functions of one or more of the above-described embodiment(s), and by a method performed by the computer of the system or apparatus by, for example, reading out and executing the computer executable instructions from the storage medium to perform the functions of one or more of the above-described embodiment(s).

The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-203357, filed Oct. 17, 2016, which is hereby incorporated by reference herein in its entirety.

What is claimed is:

1. A radiographing apparatus for identifying a contour of a predetermined target structure of a subject in an image, the radiographing apparatus comprising:
   an area setting unit configured to set a contour search area where the contour is searchable based on anatomical features of the structure of the subject;
   a contour candidate setting unit configured to set a contour candidate of the target structure; and
   a contour adjustment unit configured to adjust the contour candidate to approximate the contour candidate included in the contour search area to the contour of the target structure,
   wherein the contour candidate setting unit resets the contour candidate adjusted in the image with a first resolution as the updated contour candidate, in the image with a second resolution different from the first resolution, and
   wherein the contour adjustment unit readjusts the contour candidate in the image with the second resolution to approximate the updated contour candidate to the contour of the target structure.

2. The radiographing apparatus according to claim 1, wherein the area setting unit sets the contour search area based on at least one of a structure area indicating anatomical features of the structure of the subject, a shielded area that is shielded from radiation, and a direct irradiation area where a radiation detection apparatus is directly irradiated with radiation.

3. The radiographing apparatus according to claim 1, wherein, based on anatomical features of a structure other than the target structure, the area setting unit identifies a structure area of a structure other than the target structure, and sets the contour search area based on an area excluding the structure area.

4. The radiographing apparatus according to claim 1, wherein, based on anatomical features of the target structure, the contour adjustment unit adjusts at least one of a size, angle, and position of the contour candidate.

5. The radiographing apparatus according to claim 1, further comprising a learning unit configured to learn a texture model representing a statistical local feature of the contour of the target structure based on a pixel value profile,
   wherein the contour adjustment unit adjusts the contour candidate by comparing the local feature of the contour of the target structure of the texture model with a local feature of the contour candidate.

6. The radiographing apparatus according to claim 5, wherein the contour adjustment unit adjusts the contour candidate to a position which provides a highest similarity between the local feature of the contour of the target structure of the texture model and the local feature of the contour candidate.

7. The radiographing apparatus according to claim 1, further comprising a learning unit configured to learn a shape model representing a statistical shape of the contour of the target structure,
wherein the contour candidate setting unit sets an initial position of the contour candidate based on the shape model.

8. The radiographing apparatus according to claim 1, further comprising a learning unit configured to learn a shape model representing a statistical shape of the contour of the target structure,
wherein the contour adjustment unit smoothes the contour candidate based on the shape model.

9. The radiographing apparatus according to claim 1,
wherein the contour candidate setting unit resets the adjusted contour candidate as the updated contour candidate, and
wherein the contour adjustment unit readjusts the contour candidate to approximate the updated contour candidate to the contour of the target structure.

10. A non-transitory storage medium storing a program for causing a computer to function as each unit of the radiographing apparatus according to claim 1.

11. A radiographing system comprising:
a radiation generating unit configured to generate radiation;
a radiation detection unit configured to detect the radiation;
an area setting unit configured to set a contour search area where the contour is searchable based on anatomical features of the structure of the subject;
a contour candidate setting unit configured to set a contour candidate of the target structure; and
a contour adjustment unit configured to adjust the contour candidate to approximate the contour candidate included in the contour search area to the contour of the target structure,
wherein the contour candidate setting unit resets the contour candidate adjusted in the image with a first resolution as the updated contour candidate, in the image with a second resolution different from the first resolution, and
wherein the contour adjustment unit readjusts the contour candidate in the image with the second resolution to approximate the updated contour candidate to the contour of the target structure.

12. The radiographing system according to claim 11, wherein the area setting unit sets the contour search area based on at least one of a structure area indicating anatomical features of the structure of the subject, a shielded area that is shielded from radiation, and a direct irradiation area where a radiation detection apparatus is directly irradiated with radiation.

13. The radiographing system according to claim 11, wherein, based on anatomical features of a structure other than the target structure, the area setting unit identifies a structure area of a structure other than the target structure, and sets the contour search area based on an area excluding the structure area.

14. The radiographing system according to claim 11, wherein, based on anatomical features of the target structure, the contour adjustment unit adjusts at least one of a size, angle, and position of the contour candidate.

15. The radiographing system according to claim 11, wherein, in response to at least a part of the contour candidate or a predetermined peripheral region of the contour candidate not being included in the contour search area, the contour adjustment unit moves the contour candidate so that the contour candidate or the peripheral region is included in the contour search area.

16. A radiographing method for identifying a contour of a predetermined target structure of a subject in an image, the method comprising:
setting a contour search area where the contour is searchable based on anatomical features of the structure of the subject;
setting a contour candidate of the target structure; and
adjusting the contour candidate to approximate the contour candidate included in the contour search area to the contour of the target structure,
wherein the setting the contour candidate includes resetting the contour candidate adjusted in the image with a first resolution as the updated contour candidate, in the image with a second resolution different from the first resolution, and
wherein the adjusting the contour includes readjusting the contour candidate in the image with the second resolution to approximate the updated contour candidate to the contour of the target structure.

17. The radiographing method according to claim 16, wherein the setting the area includes setting the contour search area based on at least one of a structure area indicating anatomical features of the structure of the subject, a shielded area that is shielded from radiation, and a direct irradiation area where a radiation detection apparatus is directly irradiated with radiation.

18. The radiographing method according to claim 16, wherein, in the setting the area, based on anatomical features of a structure other than the target structure, a structure area of a structure other than the target structure is identified, and the contour search area is set based on an area excluding the structure area.

19. The radiographing method according to claim 16, wherein, in the adjusting the contour, based on anatomical features of the target structure, at least one of a size, angle, and position of the contour candidate is adjusted.

20. The radiographing method according to claim 16, wherein, in adjusting the contour, in response to at least a part of the contour candidate or a predetermined peripheral region of the contour candidate not being included in the contour search area, the contour candidate is moved so that the contour candidate or the peripheral region is included in the contour search area.

21. An image processing apparatus for identifying a contour of a predetermined target structure of a subject in an image, the image processing apparatus comprising:
an area setting unit configured to set a contour search area where the contour is searchable based on anatomical features of the structure of the subject;
a contour candidate setting unit configured to set a contour candidate of the target structure; and
a contour adjustment unit configured to adjust the contour candidate to approximate the contour candidate included in the contour search area to the contour of the target structure, wherein the contour candidate setting unit resets the contour candidate adjusted in the image with a first resolution as the updated contour candidate, in the image with a second resolution different from the first resolution, and wherein the contour adjustment unit readjusts the contour candidate in the image with the second resolution to approximate the updated contour candidate to the contour of the target structure.

22. The image processing apparatus according to claim 21, wherein, based on anatomical features of a structure other than the target structure, the area setting unit identifies a structure area of a structure other than the target structure, and sets the contour search area based on an area excluding the structure area.

23. The image processing apparatus according to claim 21, wherein, based on anatomical features of the target structure, the contour adjustment unit adjusts at least one of a size, angle, and position of the contour candidate.

24. The image processing apparatus according to claim 21, wherein the contour candidate setting unit resets the contour candidate adjusted in the image with a first resolution as the updated contour candidate, in the image with a second resolution different from the first resolution.

25. The image processing apparatus according to claim 24, wherein the contour adjustment unit readjusts the contour candidate in the image with the second resolution to approximate the updated contour candidate to the contour of the target structure.

26. The image processing apparatus according to claim 21, wherein the image is medical image.

* * * * *